United States Patent [19]

Iinuma et al.

[11] 4,318,413

[45] Mar. 9, 1982

[54] ULTRASONIC DIAGNOSTIC APPARATUS

[75] Inventors: Kazuhiro Iinuma; Kinya Takamizawa, both of Yokohama, Japan

[73] Assignee: Tokyo Shibaura Denki Kabushiki Kaisha, Kawasaki, Japan

[21] Appl. No.: 84,170

[22] Filed: Oct. 12, 1979

[30] Foreign Application Priority Data

Oct. 20, 1978 [JP] Japan ............................ 53-129386
Oct. 20, 1978 [JP] Japan ............................ 53-129387

[51] Int. Cl.³ .......................................... A61B 10/00
[52] U.S. Cl. .................................. 128/660; 128/663
[58] Field of Search .......................... 128/660–663; 73/194 A

[56] References Cited

U.S. PATENT DOCUMENTS

| 3,550,070 | 12/1970 | McLeod | 128/663 |
| 3,937,707 | 2/1976 | Kossoff | 128/663 |
| 4,062,237 | 12/1977 | Fox | 128/663 |
| 4,103,679 | 1/1978 | Aronson | 128/663 |
| 4,141,347 | 2/1979 | Green et al. | 128/663 |
| 4,182,173 | 1/1980 | Papadofrangakis et al. | 128/663 |
| 4,217,909 | 8/1980 | Papadofrangakis et al. | 128/663 |

OTHER PUBLICATIONS

Ogawa, T. et al., "B-Scan/Doppler Duplex Scanner", Nippon UTS Med. Society, 1977, pp. 183-184.

*Primary Examiner*—Robert W. Michell
*Assistant Examiner*—Francis J. Jaworski
*Attorney, Agent, or Firm*—Oblon, Fisher, Spivak, McClelland & Maier

[57] ABSTRACT

An ultrasonic diagnostic apparatus has a probe for transmitting and receiving an ultrasonic wave and an amplitude-detecting circuit, and in operation transmits an ultrasonic wave into an organism while the organism is scanned by the probe and amplitude-detects a received signal reflected from the inside of the organism, thereby to obtain a tomographic image of the organism. The ultrasonic diagnostic apparatus further includes a phase detecting circuit and an ultrasonic drive circuit. The ultrasonic drive circuit alternately supplies to the probe a first drive signal for obtaining tomographic image information and a second drive signal for obtaining blood flow information, scans in a direction of the ultrasonic wave transmission according to the first drive signal and sets the ultrasonic wave transmitting direction according to the second drive signal to a desired direction for obtaining blood flow information. Blood flows information may be obtained for a specific point, a specific line, a specific area, or for a specific area in synchronism with the organism's heartbeat. Thereby, the tomographic image information of the organism and the blood flow information as well are simultaneously obtained.

10 Claims, 32 Drawing Figures

ULTRASONIC DIAGNOSTIC APPARATUS

The invention relates to an ultrasonic diagnostic apparatus capable of providing tomographic information of a human body or the like and circulation information of blood.

Ultrasonic diagnostic apparatuses have been widely used in the medical field. Of those apparatuses, particularly the electronic scanning type apparatus can provide a tomographic image in real-time and therefore it has been used for diagnosing heart or like. A blood flow meter using Doppler effect of ultrasonic waves has also been put into practice, in which a rate of blood flow is obtained on the basis of a frequency deviation, that is, frequency difference between an ultrasonic wave transmitted and the one reflected from blood corpuscles. The blood flow meter employs continuous waves or burst waves for the ultrasonic waves. This blood flow meter fails to learn whether portions reflecting the ultrasonic wave are the blood corpuscles or other parts such as the wall of vessel or the wall of heart, and further a relation between the ultrasonic transmitting direction and the blood flow direction. This hinders the blood flow meter from measuring a real blood flow rate with a high accuracy. Moreover, since a shape of the vessel is unknown, the meter can not measure a flow amount of blood.

Figure 1:
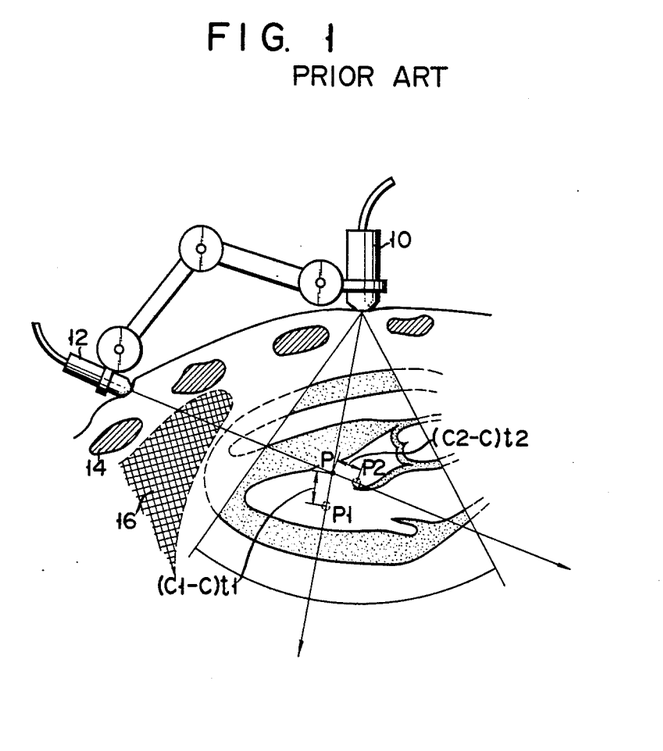
FIG. 1 shows a diagram for illustrating the operation of a conventional ultrasonic diagnostic apparatus.

To cope with the above-mentioned problems, an electronic scanning type ultrasonic diagnostic apparatus has successfully been developed in which two individual probes are provided and one of them is used for an ultrasonic pulse Doppler blood flow meter, also in view of meeting a recent requirement of tomographic images and blood flow information as well. As shown in FIG. 1 illustrating the scanning type ultrasonic diagnostic apparatus, a probe 10 for observing a tomographic image of an object to be diagnosed and another probe 12 for ultrasonic Doppler measurement are coupled with to each other by an arm and are together mounted to the diagnostic apparatus. The positions of the respective probes and the transmitting and receiving directions of the ultrasonic beam are determined by a potentiometer. The probe 10 provides a real-time tomographic image while the other probe 12 provides a flow rate of blood obtained by a Doppler effect of the ultrasonic wave. In this way, the apparatus can provide two kinds of information independently or correlatively and simultaneously.

In practical use, however, its handling is troublesome. For example, the two probes must be positioned accurately in its use. To be more specific, the heart, for example, is complicated in its shape and constantly vibrates. Accordingly, the probe, even if single, must be carefully set to permit a satisfactory diagnosis to be made for a patient. Further care must be taken for setting two probes, so that it is difficult to position two probes correlatively. In addition, to detect the set position relation it requires a relatively large arm, potentiometers, complicated arithmetic circuits and the like. This leads to a complicated construction of the apparatus.

Assume now that a position for measuring a blood flow is selected at point P on a tomogram shown in FIG. 1. Further assuming now that a set velocity of sound to obtain a tomograph image and a Doppler signal as C, an actual average velocity of sound traveling the distance from the probe 10 for tomogram to point P is denoted as C1, a time of ultrasonic wave propagating the distance from the probe 10 to point P as t1, an actual average velocity of sound. propagating the distance from the Doppler probe 12 to point P as C2, and a propagating time of the ultrasonic wave from the probe 12 to point P as t2. Since the set sound velocity for display is C, the distance from the probe 10 to point P must be Ct1 and the distance from the probe 12 to point P Ct2. Actually, however, since the average sound velocities are C1 and C2, the distances from each probes to the detecting positions are C1t1 and C2t2, respectively. Therefore, a true position of the point P to be displayed is at P1 distanced by (C1−C)t1 from the point P at the time of observing a tomographic image; it is at P2 distanced by (C2−C)t2 from the point P at the time of measuring a blood flow where C1 and C2 are greater than C. Hence, unless C1=C2=C, the Doppler signals obtained would be measured at another position from a position on the tomographic image. This causes a distortion in the position relation between the respective probes to produce an error in a correlation between them as a result of the detection. The diagnosis result varies dependent upon the direction of the ultrasonic wave emitted from the probe 12, the length of the arm connecting the probes 10 and 12 and the set value of the potentiometer.

In case where there is an organ to almost block transmission of ultrasonic wave such as rib 14, lung 16 or the like between the Doppler probe 12 and an object to be served, for example, the heart, even if the ultrasonic wave signal does not reach a target position actually, the beam direction and the target position capable of providing a tomographic image and a Doppler signal is clearly displayed by a display device in cooperation with the arm, the potentiometer, the arithmetic unit and the like. As described above, since the paths of beams emitted from the tomograph probe and the Doppler probe are different from each other, it can not be checked if the ultrasonic wave beam for measuring a blood stream reliably reaches a desired position or not.

Additionally, a careful consideration must be given to an interference between the ultrasonic signals when the tomographic observation and the measurement of blood flow are simultaneously performed.

Accordingly, an object of the invention is to provide an ultrasonic diagnostic apparatus which can provide a real time tomographic image and a blood flow rate by using the Doppler effect with a simple construction of a single probe simultaneously.

To achieve the object, there is provided an ultrasonic diagnostic apparatus having an ultrasonic probe for transmitting an ultrasonic wave in accordance with an input signal, drive means for supplying a drive signal to the ultrasonic probe to cause the ultrasonic probe to produce the ultrasonic wave, and means for amplitude-detecting or phase-detecting a signal received from the ultrasonic probe corresponding to an ultrasonic wave received by the ultrasonic probe.

Other objects and features of the invention will be apparent from the following description taken in connection with the accompanying drawings, in which.

Figure 2:
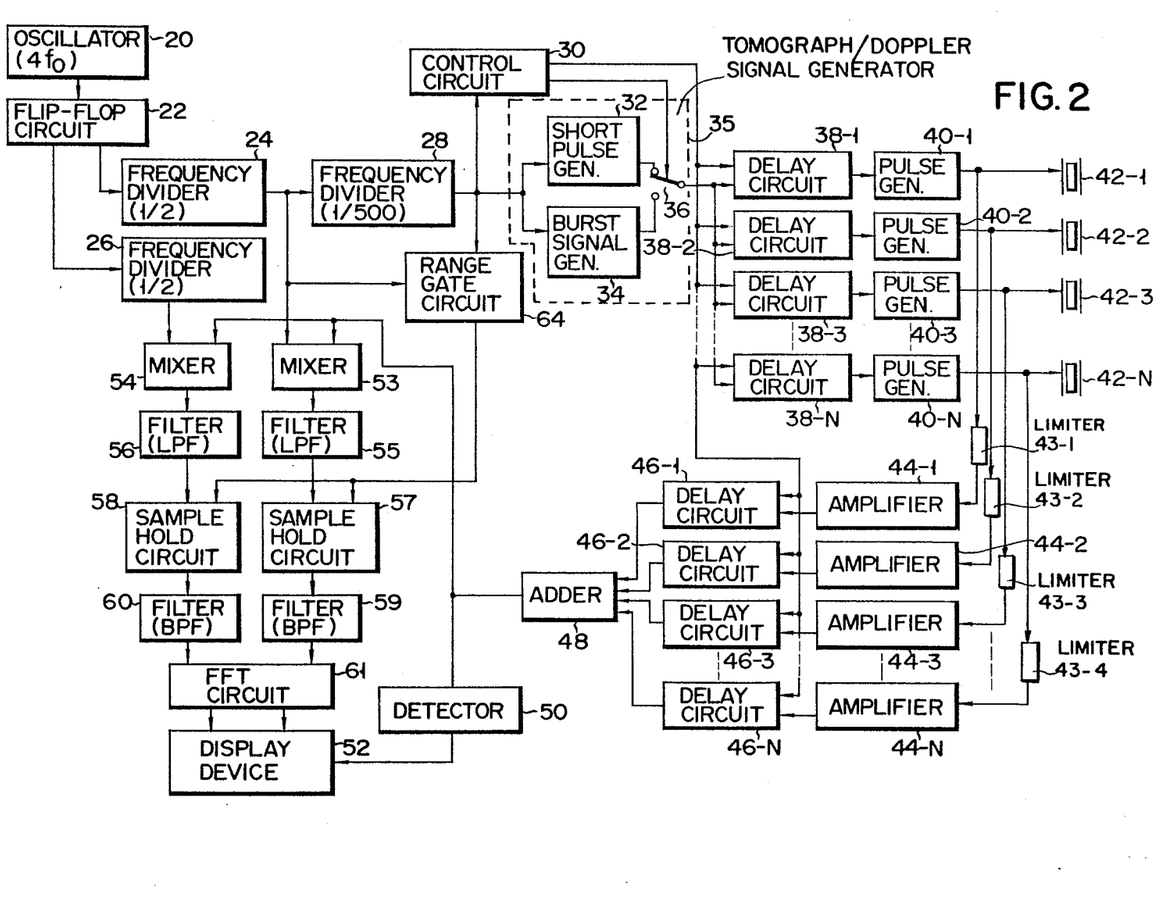
FIG. 2 shows a block diagram of an embodiment of an ultrasonic diagnostic apparatus according to the invention.

Reference is first made to FIG. 2 illustrating in block form an embodiment of an ultrasonic diagnostic apparatus according to the invention. In the figure, an oscillator 20 is a quartz crystal oscillator which produces a signal of 10 MHz ($4f_o$) with a highly stable frequency characteristic. The output signal from the oscillator 20 is applied to a flip-flop 22 which is a frequency divider. The Q output signal of the flip-flop 22 is applied to a next frequency divider 24 and $\overline{Q}$ output signal of the flip-flop 22 is applied to a next frequency divider 26. The frequency dividers 24 and 26, which are also comprised of flip-flops, frequency-divide input signals into halves, respectively. The output signals from the frequency dividers 24 and 26 have the frequencies of 2.5 MHz ($f_o$) and are different from each other by $\pi/4$ of phase. The output signal from the divider 24 is applied to a frequency divider 28 where it is frequency-divided to be 1/500. The frequency divider 28, after frequency-dividing in such a way, produces a rate signal of 5 KHz. The rate signal is applied to a control circuit 30, a short pulse generator 32, and a burst signal generator 34. The output signals from the short pulse generator 32 and the burst signal generator 34 are applied to first and second movable contacts of a switch 36, respectively. The short pulse generator 32, burst signal generator 34, and switch 36 constitute a tomograph/Doppler signal generator 35 whose output signal is switched in accordance with a control signal derived from the control circuit 30. The fixed contact of the switch 36 is connected to delay circuits 38-1 to 38-N. Delay time setting signals are applied from the control circuit 30 to the delay circuits 38-1 to 38-N. The set delay times determine the transmitting/receiving direction, i.e. a scanning direction, of the ultrasonic wave signal. A read only memory (ROM) included in the control circuit 30 has an arrangement of addresses corresponding to the scanning directions of the ultrasonic wave. Stored in the respective addresses are the delay time information necessary for the transmission and reception of the ultrasonic wave in the scanning direction. Accordingly, if an address of the ROM corresponding to a desired scanning direction is specified and selected, the ultrasonic wave signal may be transmitted in a specified scanning direction. The delay circuits 38-1 to 38-N are connected to pulse generators 40-1 to 40-N, respectively. Upon receipt of the output pulses from the pulse generators, ultrasonic vibrators, i.e. electro-acoustic converting elements 42-1 to 42-N are energized to emit ultrasonic waves. Those vibrators 42-1 to 42-N are arranged in linear fashion and disposed in a case to form an ultrasonic probe.

The ultrasonic waves transmitted enter the interior of a human body or the like and are reflected at proper organs of the interior of the human body. The reflected waves are received by the ultrasonic vibrators 42-1 to 42-N, respectively and are converted to the electronic signals. The signals are supplied to amplifiers 44-1 to 44-N through limiters 43-1 to 43-N, respectively, where they are amplified and then are applied to the delay circuits 46-1 to 46-N. The limiters 43-1 through 43-N are, for example, formed by diode limiters, which permit the received signals to pass there through and which interrupt the signals from the pulse generators 40-1 through 40-N. The delay circuits 46-1 to 46-N have delay times determined by the delay time setting signals outputted from the control circuit 30. The delay times of the delay circuits 46-1 to 46-N are selected to be the same as the corresponding ones of the delay circuits 38-1 to 38-N, respectively. The output signals from the delay circuits 46-1 to 46-N are supplied to an adder 48 where those signals are summed to form a receiving signal coming from the same direction as the transmitting ultrasonic wave. The receiving signal is amplitude-detected by a detector 50 and is applied as a tomographic information signal to a display device 52.

The receiving signal is also applied to one of the input terminals of each of mixers 53 and 54. The output signals from the frequency dividers 24 and 26 are supplied to the other input terminals of the mixers 53 and 54, respectively. In other words, the signals of the frequency $f_o$ (2.5 MHz) and with $\pi/4$-different phases are mixed with the receiving signals by the mixers 53 and 54, respectively. The mixed output signals from the mixers 53 and 54 are filtered out from filters 55 and 56 and then are supplied to sample hold circuits 57 and 58, respectively. The output signals from the sample hold circuits 57 and 58 are applied to an Fast Fourier Transformation (FFT) circuit 61 through band-pass filters 59 and 60, respectively. The FFT circuit 61 has a frequency analysis function, and outputs a positive signal when the blood flows toward the propagating direction of the ultrasonic wave or a negative signal when the blood flows away from the propagating direction of the ultrasonic wave signal. These signals are supplied to the display unit 52 where they are displayed. The display device 52 is comprised of a CRT display section and a pen recorder. The tomograph and the blood flow data are displayed on the CRT display section and the pen recorder, respectively. It is also possible to effect a display on the CRT screen in the pen recorder mode.

Output signals from the ½ frequency divider 24 and the 1/500 frequency divider 28 are applied to a range gate 64. The range gate 64 outputs a timing pulse after counting a predetermined number of output pulses from the frequency divider 24 only when the rate signal is outputted from the frequency divider 28. The receive timing of the receiving signal is proportional to a depth (distance between the probe and an observing portion, or a reflecting portion) of the observing portion. The range gate 64 can extract only the receiving signal reflected at a desired observing portion in a manner that, at the output timing of the range gate 64 with an above mentioned elasping time set up, the sample hold circuits 57 and 58 are operated to hold output signals at a given timing. The output signals from the sample hold circuits 57 and 58 are applied to the FFT circuit 61 via band-pass filters 59 and 60 to generate frequency component information, i.e. a signal proportional to the blood flow rate, which in turn is applied to the display device 52.

Figure 3A:
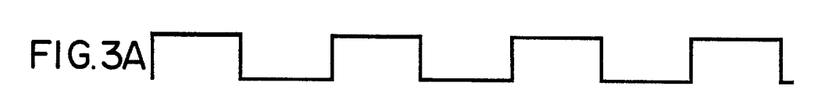
FIGS. 3A to 3I show a timing chart for useful in explaining the operation of the apparatus shown in FIG. 2.
Figure 3B:
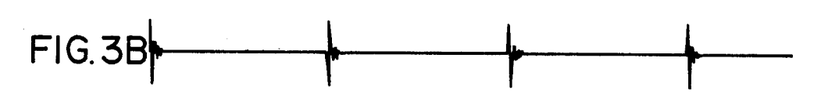
Figure 3C:
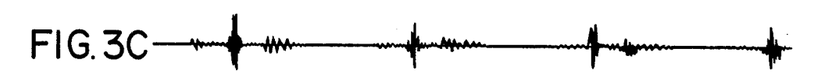
Figure 3D:
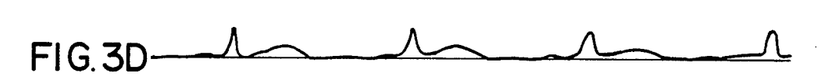

The operation of the ultrasonic diagnostic apparatus will be described with reference to FIGS. 3A to 3I illustrating wave forms of signals at the respective portions. How to obtain a tomographic image will first be given. A signal of 10 MHz outputted from an oscillator 20 is converted into a signal of 2.5 MHz by the flip-flop 22 and the frequency divider 24 and is further converted into the rate signal of 5 KHz as shown in FIG. 3A by the frequency divider 28. In synchronism with the leading edge of the rate signal, the short pulse generator 32 and the burst signal generator 34 are driven. At this time, the switch 36 has selected the short pulse generator 32, and the short pulse is delay-time controlled and is applied to the pulse generators 40-1 to 40-N. The pulse generators are driven by the single pulse, so that the ultrasonic vibrators 42-1 to 42-N, of the ultrasonic probe transmit ultrasonic waves (single pulses) every 200 μs of the rate period as shown in FIG. 3B. The center frequency $f_1$ of the ultrasonic waves transmitted is about 2.5 MHz. The transmitted ultrasonic waves are reflected at the respective portions within the human body and the reflected waves coming from the respective reflecting portions are added by the adder 48 so that the depths of the reflecting portions and the receiving timing of the received waves are related proportionally, thereby to form a receiving signal as shown in FIG. 3C. Assume now that the reflecting portion is positioned at the depth D from the probe and a propagating velocity of the ultrasonic wave within the human body is denoted as C. A time T from an instant when the ultrasonic wave emanates from the probe until it returns to the probe is given by $T=2D/C.$ The receiving signal is supplied to the detector 50 which in turn produces it as a signal containing the tomographic image information as shown in FIG. 3D and is visualized in B mode or M mode by the display device 52.

Figure 4A:
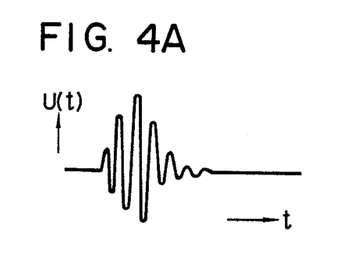
FIGS. 4A to 4D show a set of wave forms for illustrating the principle of the apparatus shown in FIG. 2.
Figure 4B:
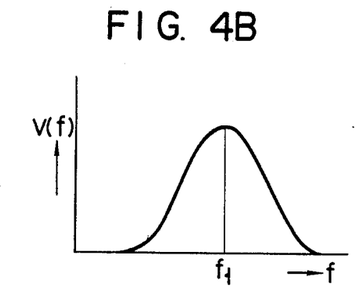
Figure 4C:
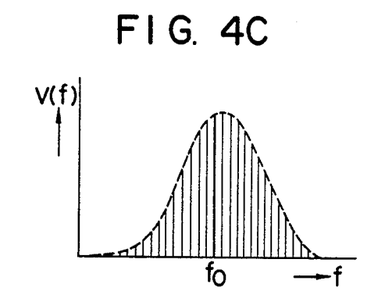
Figure 4D:
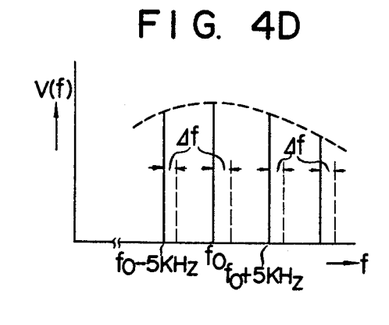

Explanation will be given of how to obtain the blood flow information. The reflecting signal of the short pulse ultrasonic wave reflected at a fixed reflecting member is generally as shown in FIG. 4A. The frequency spectrum of the reflecting signal is as shown in FIG. 4B. As shown, the frequency components of the signal distribute over a wide frequency range with its center frequency $f_1$ (about 2.5 MHz). Therefore, it is very difficult to detect a slight Doppler deviation of 1 KHz by using such a reflecting signal. As in the present invention, however, when the short pulse ultrasonic wave, as shown in FIG. 4C, transmitted is repeatedly driven by the rate signal of 5 KHz obtained by frequency-dividing an output signal produced from the high accuracy oscillator 20, the frequency spectra of its reflecting wave has an envelope equivalent to the frequency spectra of the reflecting signal of a short pulse and takes the form of line spectra of the frequency integer times 5 KHz. The pulse generators 40-1 to 40-N, and the amplifiers 44-1 to 44-N have slight time delays and the delay times of the delay circuits vary slightly with the scanning directions. However, this is not problematic since the pulse intervals are always equal in a given scanning direction. A diagram when the abscissa of FIG. 4C is enlarged is illustrated in FIG. 4D. In the figure, continuous lines indicate reflecting wave spectra reflected at fixed reflecting body and chain lines indicate the reflecting wave spectra reflected from a moving body with a Doppler deviation of Δf. Therefore, by mixing the receiving signal with the signal of $f_o$ (2.5 MHz) and extracting a difference therebetween, one can detect the Doppler deviation frequency. Unless the frequency divider 28 accurately frequency-divides the reference signal into 1/500 thereby to produce a rate signal, it is very difficult to extract the Doppler deviation frequency.

Figure 5A:
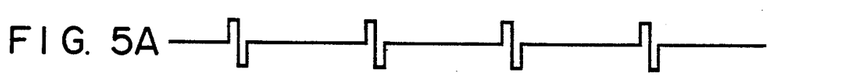
FIGS. 5A to 5G show a set of wave forms for illustrating a transmitting ultrasonic wave.
Figure 5B:
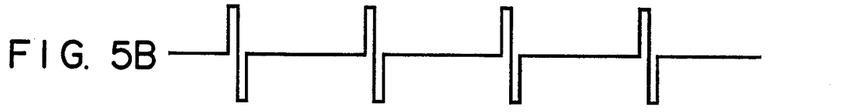
Figure 5C:
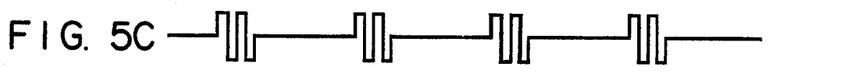
Figure 5D:
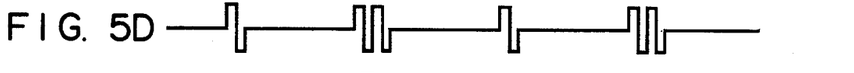

A short pulse may be used for observing the blood flow. Preferably, a short pulse as shown in FIG. 5A is used for the tomogram observation and a pulse with a large amplitude as shown in FIG. 5B or a burst signal with the increased number of waves as shown in FIG. 5C or a mixed signal mixing a short pulse and a burst signal as shown in FIG. 5D is used for the blood flow measurement. If it does so, it may be prevented that the intensity of the reflecting wave becomes extremely smaller at the time of measurement of blood flow, in a manner that the powerful reflecting wave from blood corpuscles is used for the blood flow measurement and the weak reflecting wave from lung or muscle for the tomogram observation. The use of such a powerful signal never brings about degradation of the distance resolution about the tomogram and improves the S/N ratio in the blood flow measurement, even if the blood flow measurement and the tomogram observation are performed simultaneously.

Figure 3E:
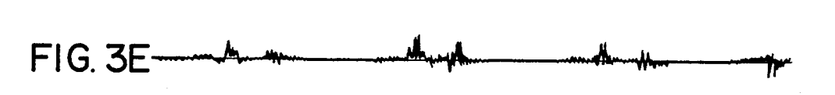
Figure 3F:
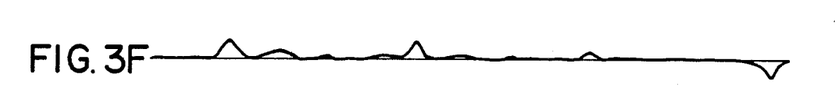
Figure 3G:
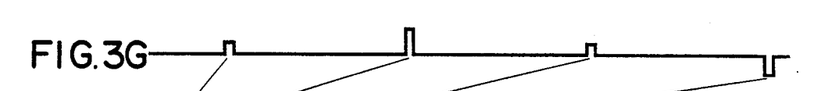
Figures 3H, 3I:
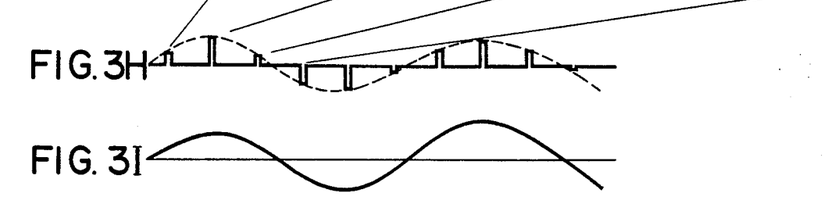

It is for this reason that, at the time of blood flow measurement, the switch 36 is switched to the burst wave generator 34 side, and the delay times of the delay circuits 38-1 to 38-N and 46-1 to 46-N are so fixed that the direction of the ultrasonic wave emitted from the probe 42 is fixed. The receiving signal thus obtained shown in FIG. 3C (the output signal from the adder 48) is applied to the mixer 53 and is mixed with a reference signal of 2.5 MHz derived from the frequency divider 24 to produce a mixed output signal as shown in FIG. 3E. The mixed output signal is filtered by the low-pass filter 55 to be a signal as shown in FIG. 3F which in turn is applied to the sample hold circuit 57. Then the sample hold circuit 57 sequentially holds the low-passed output signal shown in FIG. 3F after a fixed time T delayed from the leading edge of the rate signal by the range gate 64. The Doppler deviation component of the reflecting wave reflected at the reflecting portion at a given depth is obtained as a sampling signal shown in FIG. 3G. The pulse train of FIG. 3G is illustrated when the axis of the signal is compressed as illustrated in FIG. 3H. Further, by filtering the signal by the bandpass filter 59 a Doppler signal (a signal proportional to the blood flow rate) as shown in FIG. 3I may be obtained.

When the operations are alternately performed during successive rate signals, the information relating to the tomogram and the information relating to the blood flow may simultaneously be obtained. Assume now that the scanning directions transmitted or received by the probe 42 are denoted as 1, 2, ..., k, ..., 64, and a blood flow at a position P in the direction K is measured. On this assumption, the scanning direction K is specified by the ROM of the control circuit 30 every other rate period such as "1, k, 2, k, ... 63, k, 64" and at the other timings of the rate signal the scanning direction is sequentially specified from "1". If it does so, the Doppler signal is obtained at the time of the scanning in the direction K. At the time of the scanning in the sequential directions, the B mode signal may be obtained. In other words, the blood flow measurement and the tomogram observation are performed simultaneously. At this time, the effective rate frequency of the ultrasonic wave signal for the tomogram observation and the blood flow measurement is ½ of the rate frequency as mentioned above, that is, 2.5 KHz.

The reason for this will be described hereinafter. The following relations hold among the Doppler frequency $f_{rd}$, the average sound velocity of the ultrasonic wave signal D, the maximum visual field depth Dmax, the maximum detection speed Vm, the maximum Doppler shift frequency $\Delta f_{max}$, and a transmitting carrier frequency $f_o$ of the ultrasonic signal.

$$f_{rd} < C/2Dmax \qquad (1)$$

$$\Delta f_{max} \leqq f_{rd}/2 \qquad (2)$$

$$\Delta f_{max} = 2f_o Vmax/C \qquad (3)$$

The equation (2) is derived from the sampling theorem. Vmax is the velocity of the blood flow in the ultrasonic wave transmission and reception. From the equations (2) and (3), we have $$f_{rd} > 4f_o Vmax/C \qquad (4)$$

where $f_o = 2.5$ MHz.

$C = 1.5 \times 10^6$ mm/sec and when the Vmax is set to 30 cm/sec on the basis the general specification of the diagnostic apparatus, the Doppler frequency $f_{rd}$ must be set to 2 KHz or more. Since the rate frequency $f_r$ is 5 KHz, if the Doppler rate frequency $f_{rd}$ is set to 2.5 KHz, the above-mentioned requirement is satisfied.

Figure 5E:
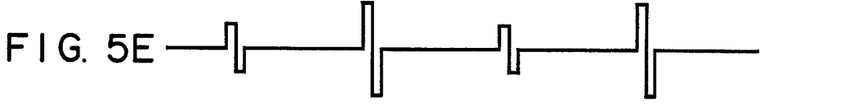

Further, if the output signal of the range gate circuit 64 is supplied to the display device 52, the received signal of the probe 42 is intensity modulated at the sampling timing of the range gate circuit 64 and then displayed, whereby a position for the blood flow measurement may be clearly displayed on a tomogram. Accordingly, by switching the switch 36 in accordance with the scanning direction switched for each given rate signal by the control circuit 30 to transmit an ultrasonic wave signal as shown in FIG. 5D (as shown, a single pulse and a burst signal appear alternately) or as shown in FIG. 5E (as shown, a single pulse and a single pulse with a large amplitude), both the tomogram information and the blood flow information are obtained in the form of signals with high distance resolution and high S/N ratio. Of course, each rate frequency is ½ $f_r$ and the range gate 64 is operated by the Doppler rate pulse (2.5 KHz).

Generally, ultrasonic pulses are transmitted at relatively long intervals. That is, if the rate frequency is sufficiently lowered, each ultrasonic pulse is transmitted when substantially all reflected waves including waves reflected from side-lobes and waves reflected in various directions cease to exist. In this case, each pulse wave reflected is rarely mixed with the preceding pulse wave. (Hereinafter a pulse wave mixed with the preceding pulse wave is called "superposed wave"). However, the lower is the rate frequency, the fewer ultrasonic pulses are transmitted in a given period of time, and hence the fewer scanning lines. This means that it takes longer to obtain one image. If a longer time cannot be used to form one image, the number of scanning lines cannot help but be reduced. If fewer scanning lines are used, the quality of the resultant image will be deteriorated. The rate frequency cannot therefore be lowered too much. At the same, it cannot be elevated since if it is elevated, more superposed waves and hence more noise will be generated.

Noise becomes very problematical if a tomogram and blood flow data are to be obtained at the same time. To examine, for example, the heart, waves reflected from the cardiac muscle are detected to obtain a tomogram whereas waves reflected from the blood corpuscles are detected to learn the blood flow in the heart. The voltage of the Doppler signals from the blood corpuscles, i.e. the waves reflected from the blood corpuscles, is extremely low, approximately 1/100 to 1/1000 of the voltage of the waves reflected from the cardiac muscle. There is a great risk that each waves reflected from the blood corpuscles would be affected by the preceding wave reflected from the cardiac muscle.

With the Doppler apparatus for obtaining data about a blood flow, the signals from a stationary object are not detected at all, and superposed waves, if any, due to waves reflected from the cardiac muscle in various directions, can be regarded as waves reflected from a stationary object. If a tomogram and blood flow data are to be obtained at the same time, the ultrasonic beam is emitted in various directions so as to obtain a tomogram of the heart even if the cardiac muscle is substantially not moving. Thus, the distance between the probe and the cardiac muscle is varying all the time, and the cardiac muscle appears as if moving. Consequently, a phenomenon similar to Doppler effect takes place, and signals caused by the phenomenon mingle with the necessary Doppler signals and adversely function as noise.

Figure 5F:
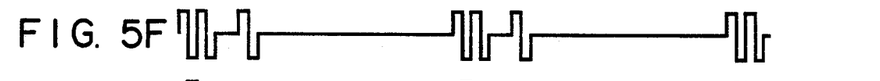
Figure 5G:
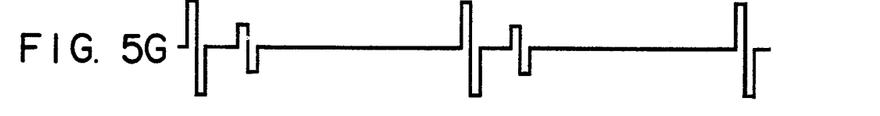
Figure 6:
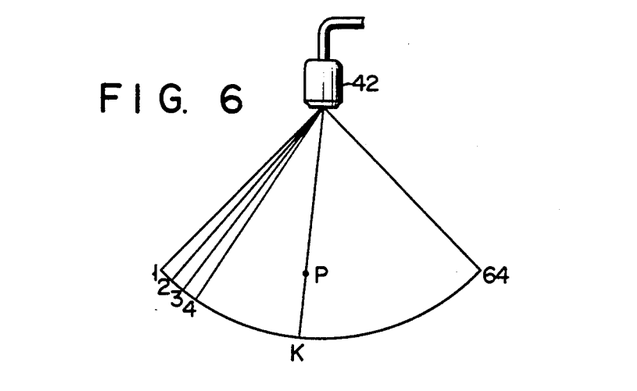
FIG. 6 shows a diagram illustrating a probe and its ultrasonic transmitting and receiving direction.

As mentioned above, the voltage of the waves reflected from blood corpuscles is much lower than that of the waves reflected from the cardiac muscle. If the rate pulse intervals remain unchanged, each wave reflected from the cardiac muscle is scarcely affected by the preceding wave reflected from the blood corpuscles, though each wave reflected from the blood corpuscles is much affected by the preceding wave reflected from the cardiac muscle. Therefore, the interval between a pulse for obtaining a blood flow data and the immediately succeeding pulse for obtaining a tomogram is made shorter than the interval between each pulse for obtaining a tomogram and the immediately succeeding pulse for obtaining a blood flow data, as illustrated in FIG. 5F and FIG. 5G.

The embodiment thus far described may measure the blood flow only at one place on a single scanning line (ultrasonic beam). The present invention allows the blood flow to simultaneously be measured at a plurality of places on a single scanning line.

Figure 7:
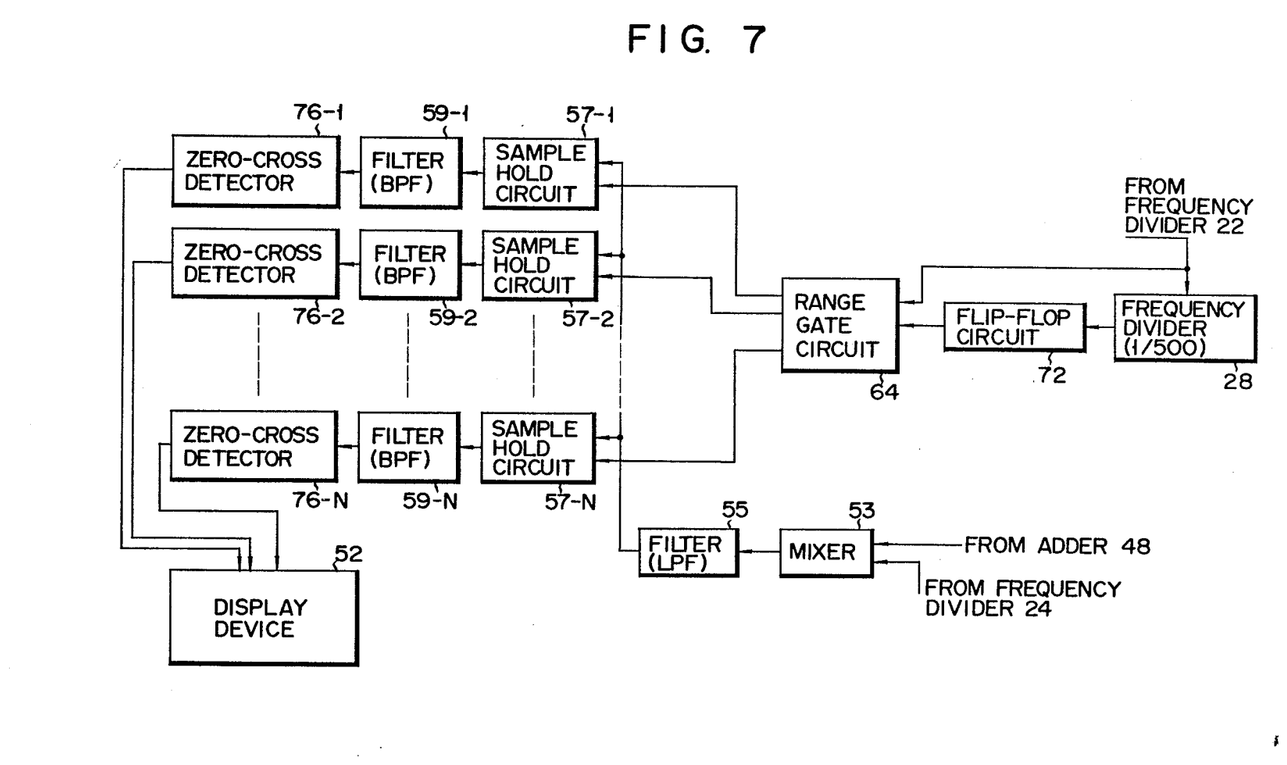
FIG. 7 shows a block diagram of a second embodiment of an ultrasonic diagnostic apparatus according to the invention.

An embodiment implementing this is in block form illustrated in FIG. 7 in which like symbols designate like or equivalent portions in FIG. 2 already described, for simplicity. Compared to the embodiment of FIG. 2, the FIG. 7 embodiment features a parallel arrangement of circuitries (each including sample hold circuit 57 and the band-pass filter 59) each arranged downstream of the frequency divider 28. An output signal (rate signal of 5 KHz) is coupled with a flip-flop 72 which is so gate-controlled as to output a signal only at the time when the control circuit 30 (FIG. 2) specifies the scanning direction K. Through the action of the flip-flop 72, the rate signal is supplied to the range gate 64 with the output signal of the frequency divider 22 only at the time of the transmitting/receiving ultrasonic wave signal in the scanning direction K, i.e. at the time of the blood flow measurement. The output signal (return signal) of a filter 55 is applied to the signal input terminals of the sample hold circuit 57-1 to 57-N. The output signals of the sample hold circuit 57-1 to 57-N, respectively, are supplied to the display unit 52, through band-pass filters 59-1 to 59-N, and zero-cross detectors 76-1 to 76-N.

Figure 8A:
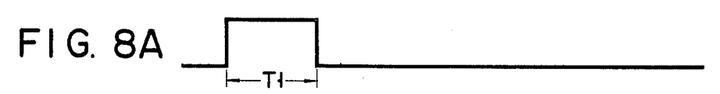
FIGS. 8A to 8F show a set of timing diagrams useful in explaining the operation of the second embodiment.
Figure 8B:
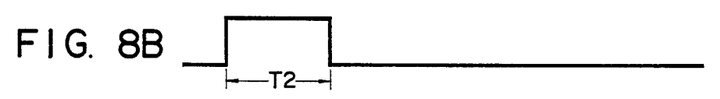
Figure 8C:
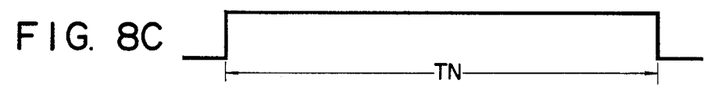
Figure 8D:
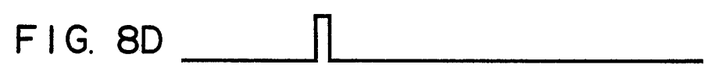
Figure 8E:
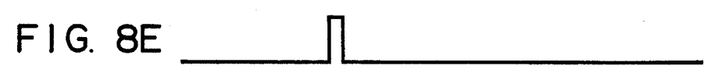
Figure 8F:
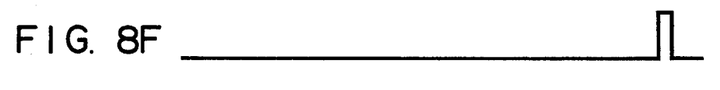

The operation of the FIG. 7 embodiment will be described with reference to FIGS. 8A to 8F. At the time of the blood flow measurement, in response to the rate signal outputted from the flip-flop 72, pulsate signals with widths $T_1$ to $T_N$ as shown in FIGS. 8A to 8C are generated in the range gate 64. At the trailing edges of those pulsate signals, the range gate 64 produces timing pulses with a fixed width as shown in FIGS. 8D to 8F. Only at the time periods that those timing pulses are outputted, the sample hold circuits 57-1 to 57-N are holded to permit the receiving signals to be applied to the display unit 52 via band-pass filters 59-1 to 59-N.

Here, it is assumed that the number of channels, or the circuitries as mentioned above, are 33, that the outputting time periods $T_1$ to $T_N$ are 26 μs, 30 μs, ... 154 μs, respectively, and that the time width of the time pulse is 4 μs.

With this circuit construction, the receiving signals inputted through the filter 55 to the sample hold circuit 57-1 to 57-N are sequentially sampled corresponding to the depths of the interval organs from the probe. To be more specific, if the sample hold circuit 57-1 samples a return signal reflected at a point in the depths 20 mm from the probe, the succeeding sample hold circuits 57-2 to 57-N sample return pulses from the points in depths 23 mm, 26 mm..., 116 mm. In other words, the return signals are sampled with intervals of 3 mm. The received information is inputted through the band-pass filters 59-1 to 59-N to the zero-cross detectors 76-1 to 76-N, respectively. The zero-cross detectors 76-1 to 76-N detects the zero-cross points of those signals sampled to obtain the Doppler deviation frequencies. Those Doppler deviation frequencies are subjected to a frequency to voltage conversion, for example, to be converted into signals with amplitudes proportional to a velocity of the blood flow, which in turn are applied to the display unit 52. Here, it is only necessary to use the zero-cross detectors 76-1 to 76-N which permit counting the number of zero-crossing of the signal for a given period of time. A frequency analyzer may be substituted for those zero-cross retectors. With the above-mentioned construction, the Doppler deviation information, i.e. the blood flow information, may be simultaneously observed at a plurality of places from a single ultrasonic receiving signal. There is provided also another method to observe at a plurality of places the Doppler deviation information which is called MTI (moving target information) method. In this method, the phase detected signals are subtracted from each other using one rate delay time. The direction of the blood flow is obtained through the phase comparison as in the first embodiment.

Another embodiment enabling the blood flow to simultaneously be measured at a plurality of places will be described. A major part of the implementation of such is in block form illustrated in FIG. 9. The output signal (rate signal) of the frequency divider 28 also used in the first embodiment is inputted to a flip-flop 80. And, only when the control circuit 30 (FIG. 2) specifies the scanning direction K, the output signal of the flip-flop 80 is set to "1" to permit the rate signal of 2.5 KHz to pass therethrough to a RAM 82 as a scanning control signal. The Doppler deviated receiving signal coming through the filter 55 is written into the corresponding address of the RAM 82 after it is converted into a digital signal by the A/D converter 84. The sampling period of the A/D converter 84 and the periods of write and read to be described later are controlled by a clock signal of 400 KHz generated by the clock generator 86. The signal read out from the RAM 82 is inputted to a memory 96 through a D/A converter 88, a filter 90, a zero-cross detector 92 and an A/D converter 94. By the clock signal of 6.25 KHz obtained by 64 frequency-dividing the clock signal derived from the clock generator 86 through the frequency-divider 98, the receiving signal is written into the memory 96. Then, the Doppler signal written into the memory 96 is read out by the clock signal of 400 KHz, and then is converted into an analog signal (amplitude variation signal) by the D/A converter 100. The converted one is applied to the display device 52 where it is intensity-modulated and visualized. The display device 52 is so designed that the intensity-modulated signal is swept by using the rate signal from the frequency divider 28.

Figure 9:
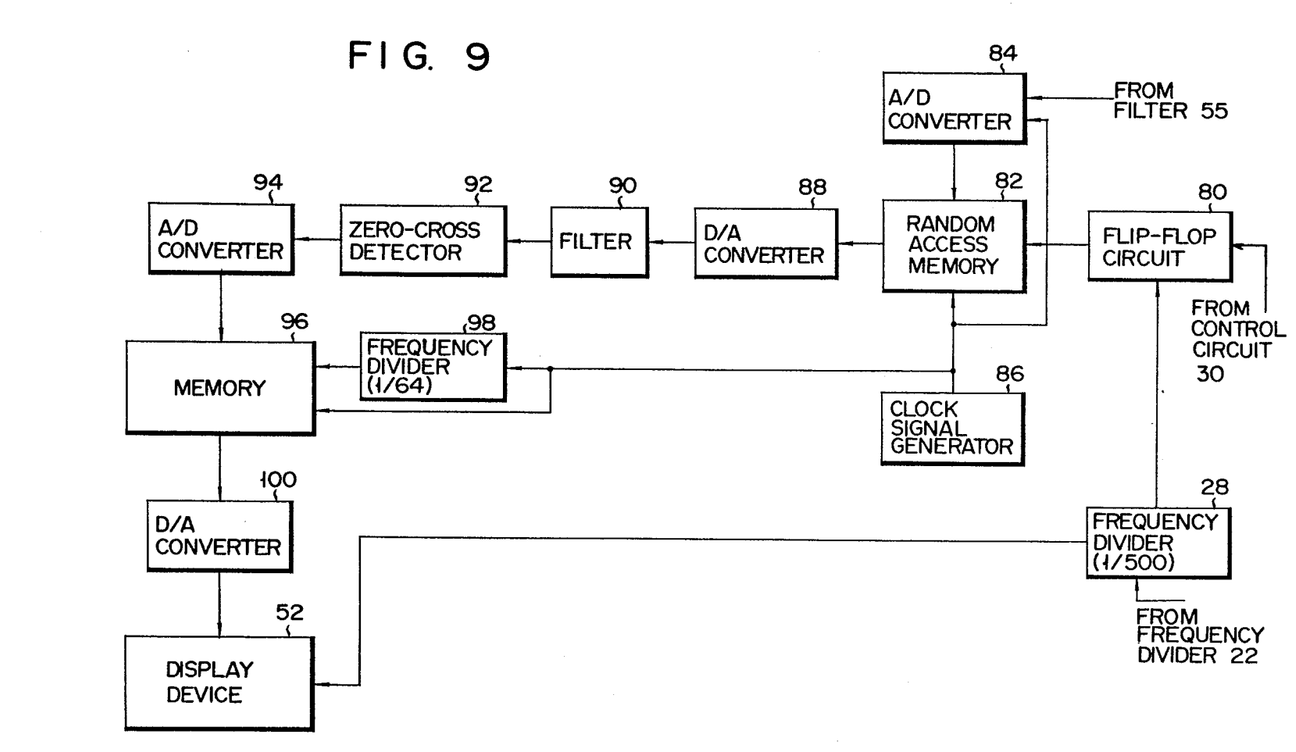
FIG. 9 shows a block diagram of a third embodiment of the ultrasonic diagnostic apparatus according to the invention.

The operation of the third embodiment described above will be given. Here, when the probe has 64 scanning directions as shown in FIG. 5, the RAM 82 has addresses of 64×64. The Doppler information obtained by the first transmission of the ultrasonic wave is written into addresses on the first row of the RAM 82 (1, 1), (1, 2), ... (1, 64). The Doppler information obtained by the second transmission is loaded into the addresses on the second row (2, 1), (2, 2), ... (2, 64). Similarly, the Doppler information by the 64th transmission is written into the addresses (64, 1), (64, 2), ... (64, 64). The time taken for the information of one scanning to be written into the addresses on one row is 160 μs since the frequency of the write clock signal is 400 KHz and the number of the addresses on one row is 64. This time corresponds to approximately 0 to 12 cm of the depths of the observing or diagnostic portions by one transmission of the ultrasonic wave. Since the Doppler scanning and the B mode scanning of the tomographic observation are alternately performed at the rate period of 400 μs, 25.6 ms is taken for the information to be written into all the addresses of 64 rows. The positions of the addresses on the respective rows correspond to the depths of the observing portions.

The information written into the RAM 82 every row are read out every column. For example, the information in the addresses (1, 1), (2, 1), ... (64, 1) on the first column are read out and then the information in the addresses (1, 2), (2, 2), ... (64, 2). The information read out of one column indicate the elapse of time of a signal Doppler-deviated at the same depth, i.e. the same observing portion. Therefore, from the information of each column, the Doppler signal for each column may be made when the information is restored to its original form by the D/A converter 88, the restored one is smoothed by the filter 90 and then is subjected to a zero-cross detection by the zero-cross detector 92. The result of the zero-cross detection is the Doppler signal. In this case, since the read period for one column of the RAM 82 is 160 μs, the read time for reading out the Doppler signal at one observing position is 160 μs×64, i.e. 10.24 ms.

When the display device 52 receives the Doppler signals from the respective observing portions, it displays the velocity of the blood flow at each observing portion in the form of the intensity information intensity-modulated. In an alternation, the output signals from the RAM 82 are subjected to a Fast Fourier Transformation for the frequency analysis and the result of the frequency analysis is directly loaded into the memory 96. The direction of the blood flow may be obtained by the phase comparison, as in the first embodiment.

In the third embodiment, the lapse of time of the blood flow information depends on the scanning time of the probe but not on heart beat, for example. To solve the problem, another embodiment was proposed in which another memory and an electro-cardiograph are additionally used and the Doppler observation is performed in synchronism with heart beat to measure a change of the blood flow rate during one heart beat. This is partly illustrated in FIG. 10 as a fourth embodiment. As shown, the output signal from the RAM 82 shown in FIG. 9 is inputted to the digital zero-cross detector 102 which in turn produces it as a Doppler signal for writing to the RAM 104. The read and write operations for the RAM 104 are controlled by the clock signal of 400 KHz outputted from the clock generator 86. The timing of the write operation is synchronized with an R wave extracted from the electro-cardiograph 106 through a wave shaping circuit 108.

Figure 10:
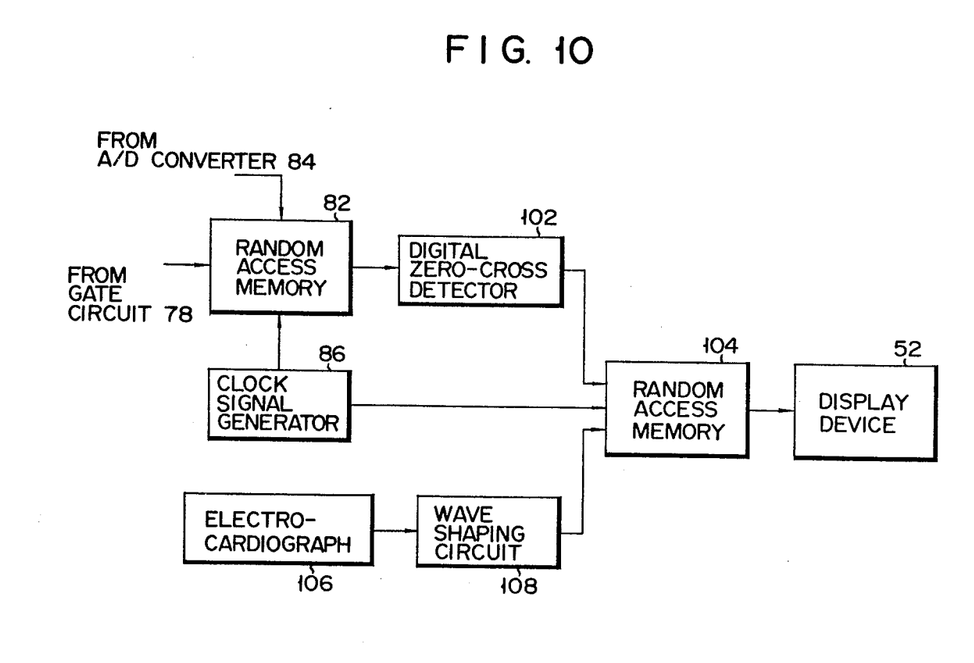
FIG. 10 shows a block diagram of a fourth embodiment of the ultrasonic diagnostic apparatus according to the invention.

As in the third embodiment, the scanning directions of the probe are 64 and the RAM 104 has addresses $64 \times 64 \times 64$. When the R wave of the first heart beat is obtained from the electro-cardiograph, the Doppler signal read out from the RAM 82 for each column is written into the RAM 104. The Doppler information read out from the addresses (1, 1), (2, 1), ... (64, 1) on the first column of the RAM 82 are written into the address (1, 1, 1) on the first column of the RAM 104; the information from the addresses (1, 2), (2, 2), ... (64, 2) on the second column to the address (1, 1, 2). Similarly, the Doppler signal obtained from the information stored in the addresses (1, 64), (2, 64), ... (64, 64) on the 64th column is written into the address (1, 1, 64). The time taken for the writing operations is equal to 25.6 ms of the rate period.

At the next rate period, the Doppler signals read out from the RAM 82 are written into the addresses (2, 2, 1), (2, 2, 2), ... (2, 2, 64) of the RAM 104. Similarly, the Doppler signal from the RAM 82 are successively written into the addresses (3, 3, 1), (3, 3, 2), ... (3, 3, 64).

When the R wave of the second heart beat is detected from the cardiograph 106, the Doppler signals are successively loaded into at first to the addresses (1, 2, 1), (1, 2, 2), ... (1, 2, 64), then to the addresses (2, 3, 1), (2, 3, 2), ... (2, 3, 64), and finally to the addresses (64, 1, 1), (64, 1, 2), ... (64, 1, 64). In this way, when the 64 heart beats are detected, the Doppler signals are written into all the addresses of the RAM 104. In this way, the blood flow velocity information at different portions of a tomogram at the input timing of the heart beat are loaded into the first memory area of the RAM 104 including the addresses (1, 1, 1) to (1, 64, 64). The blood flow velocity information after one rate period (25.6 ms) from the input timing of the heart beat are loaded into the second memory area including the addresses (2, 1, 1) to (2, 64, 64). Similarly, the blood flow velocity information corresponding to the lapse of time (of the expansion and contraction of the heart) are written into the succeeding memory areas for the addresses (64, 1, 1), to (64, 64, 64).

When the address area of the RAM 104 is specified in accordance with a condition of the heart contraction by the tomographic information obtained by the B mode scanning to read out the Doppler signals from the specified memory area, and those read out signals are displayed the image indicates the blood flow velocity information in a state of the tomogram displayed. In displaying the information, the tomogram is intensity-modulated and displayed with white color, and the positive and the negative directions of the blood flow velocity are colored red and blue in similar way.

To improve the accuracy of the information, the above-mentioned measurements are performed several times to obtain the average of the measuring results since the heart does not necessary move in exactly the same way for the respective beats. The Doppler signals in the respective memory areas of the RAM 104 represent the information every 25.6 ms, so that the velocity of the blood flow is read out and displayed as a change for each 25.6 ms. Therefore, 160 KHz or more is sufficient in use for the read clock frequency of the RAM 104. Accordingly, 200 KHz or 400 KHz, for example, are satisfactory for reading out of the RAM 104.

Additionally, if the scanning direction for the Doppler observation is variable, the blood flow measurement over the entire area of the tomogram may be possible.

As described above, the ultrasonic diagnostic apparatus according to the invention can measure a movement of the heart and a change of the blood flow at that time as well, so that the apparatus is useful for the diagnosis of the circulatory system.

It is evident that the present invention is not limited to the above-mentioned embodiments. For example, the ultrasonic wave to obtain the tomogram may be a short burst signal with several wave lengths to ensure a satisfactory distance resolution. Further, the linear scanning may be used in place of the sector scanning employed in the above embodiments. The frequency of the rate signal, the period of the read and write operations for the memory may be selected case by case.

What we claim is:

1. An ultrasonic diagnostic apparatus comprising:
   means for generating a clock pulse signal;
   means for dividing the clock pulse signal to generate a rate signal;
   a single ultrasonic probe including a plurality of electro-acoustic converting elements for transmitting an ultrasonic wave in response to a drive signal supplied thereto;
   drive means for alternately supplying to said ultrasonic probe a first drive signal for obtaining tomographic image information and a second drive signal for obtaining blood flow information, the timing in which these drive signals are supplied to the ultrasonic probe being in synchronism with the rate signal;
   means for amplitude-detecting a receiving signal when said probe receives a reflecting ultrasonic wave corresponding to the first drive signal;
   means for phase-detecting a receiving signal when said probe receives a reflecting ultrasonic wave corresponding to the second drive signal, the phase detection being effected based on a difference in frequency between the clock pulse signal and the receiving signal; and
   means for displaying a tomographic image obtained from said amplitude-detecting means and blood flow information obtained from said phase-detecting means.

2. An ultrasonic diagnostic apparatus according to claim 1, wherein said drive means includes means for scanning in a direction of the ultrasonic wave transmission for obtaining tomographic information and for setting the ultrasonic wave transmitting direction to a desired direction for obtaining blood flow information.

3. An ultrasonic diagnostic apparatus according to claim 1, wherein said drive means includes means for making the interval between the first drive signal and the immediately succeeding second drive signal longer than the interval between the second drive signal and the immediately succeeding first drive signal.

4. An ultrasonic diagnostic apparatus according to claim 1, wherein said phase detecting means includes a zero-cross detector for detecting a zero-cross timing of a received signal.

5. An ultrasonic diagnostic apparatus according to claim 1, wherein said phase detecting means includes a gate circuit to be enabled for a given time when it receives a control signal, and a gate control circuit to supply a control signal to said gate circuit after a given time since said drive means begins to supply the second drive signal, whereby said phase detecting means phase-detects a receiving signal derived from said probe through said gate circuit.

6. An ultrasonic diagnostic apparatus according to claim 1, wherein said phase-detecting means includes a plurality of gate circuits to be enabled for a given time when those gate circuits receive a control signal, and a plurality of gate control circuits for supplying control signals to said gate circuits after given different times since said drive means begins to supply the second drive signal, whereby said phase detecting means phase-detects receiving signals derived from said probe through said gate circuits.

7. An ultrasonic diagnostic apparatus according to claim 1, wherein said probe is provided with a plurality of electro-acoustic converting elements linearly arranged, and said drive means includes a plurality of delay circuits connected to said electro-acoustic converting elements and a delay control circuit for supplying signals to set delay times to said delay circuits.

8. An ultrasonic diagnostic apparatus according to claim 1, wherein said phase detecting means includes a memory to which a receiving signal derived from said probe is loaded when said drive means supplies the second drive signal, and a control circuit for reading out the loaded information from said memory after a given time since said drive means begins to supply the second drive signal, whereby said phase-detecting means phase-detects the information read out.

9. An ultrasonic diagnostic apparatus according to claim 1, wherein said phase-detecting means further includes a cardiograph, and said read-out control circuit reads out the information from said memory in synchronism with an R wave of said cardiograph.

10. An ultrasonic diagnostic apparatus according to claim 1, wherein said clock pulse generating means produces two pulse signals whose phases are different from each other by 90°, said means for dividing having a frequency divider and said phase-detecting means having two mixers to each of which the pulse signal and receiving signal are supplied, the mixer producing a difference in frequency between the pulse signal and receiving signal.

* * * * *